United States Patent [19]

Godiska et al.

[11] Patent Number: 5,688,927

[45] Date of Patent: Nov. 18, 1997

[54] MACROPHAGE DERIVED CHEMOKINE

[75] Inventors: Ronald Godiska, Bothell; Patrick W. Gray, Seattle, both of Wash.

[73] Assignee: ICOS Corporation, Bothell, Wash.

[21] Appl. No.: 480,449

[22] Filed: Jun. 7, 1995

[51] Int. Cl.$^6$ .................. C07K 16/22; C07K 16/24; C07K 16/26

[52] U.S. Cl. ............... 530/388.23; 530/388.1; 530/388.24; 530/388.25; 435/335; 435/336; 435/331

[58] Field of Search .............. 530/388.23, 388.1, 530/388.24, 388.25, 389.2; 435/240.27, 335, 336, 331

[56] References Cited

U.S. PATENT DOCUMENTS

| | | |
|---|---|---|
| 4,965,392 | 10/1990 | Fritzberg et al. .................. 558/254 |
| 5,037,630 | 8/1991 | Fritzberg et al. .................. 424/1.1 |
| 5,179,078 | 1/1993 | Rollins et al. ......................... 514/2 |
| 5,241,049 | 8/1993 | Goodman et al. .................. 530/350 |
| 5,278,287 | 1/1994 | Rollins et al. ....................... 530/351 |
| 5,413,778 | 5/1995 | Kunkel et al. ..................... 424/1.41 |

FOREIGN PATENT DOCUMENTS

| | | |
|---|---|---|
| 0 310 136 A2 | 4/1989 | European Pat. Off. . |
| WO 95/13295 | 5/1995 | WIPO . |
| WO 95/17092 | 6/1995 | WIPO . |

OTHER PUBLICATIONS

Ahuja, et al., "Molecular Evolution of the Human Interleukin-8 Receptor Gene Cluster," *Nature Genetics*, 2:31-36 (Sep., 1992).

Altschul, et al., "Basic Local Alignment Search Tool," *J. Mol. Biol.*, 215:403-410 (1990).

Baggiolini, et al., "Interleukin-8 and Related Chemotactic Cytokines—CXC and CC Chemokines," *Advances in Immunology*, 55:97-179 (1994).

Better et al., "Escherichia coli Secretion of an Active Chimeric Antibody Fragment," *Science*, 240:1041-43 (May 20, 1988).

Bitter, et al., "Secretion of foreign proteins from Saccharomyces cerevisiae directed by α-factor gene fusions," *Proc. Natl. Acad. Sci. USA*, 81:5330-5334 (Sep., 1984).

Brown, et al., "A Family of Small Inducible Proteins Secreted by Leukocytes are Members of a New Superfamily that Includes Leukocyte and Fibroblast-Derived Inflammatory Agents, Growth factors, and Indicators of Various Activation Processes," *J. Immunology*, 142(2):679-687 (Jan. 15, 1989).

Chang, et al., "Cloning and expression of a λ-interferon-inducible gene in monocytes: a new member of a cytokine gene family," *International Immunology*, 1(4):388-397 (1989).

Chang, "Thrombin Specificity," *Eur. J. Biochem.*, 151:217-224 (1985).

Charo, et al., "Molecular cloning and functional expression of two monocyte chemoattractant protein 1 receptors reveals alternative splicing of the carboxyl-terminal tails," *Proc. Natl. Acad. Sci., USA*, vol. 91:2752-2756 (Mar., 1994).

"Chemokines" in *R&D Systems 1995 Catalog*, R&D Systems, Minneapolis, MN pp. 80-85.

Chen et al., "High-Efficiency Transformation of Mammalian Cells by Plasmid DNA," *Mol. Cell. Biol.*, 7(8):2745-2752 (Aug. 1987).

Chen, et al., "Calcium Phosphate-Medicated Gene Transfer: A Highly Efficient Transfection System for Stably Transforming Cells with Plasmid DNA," *BioTechniques*, 6(7):632-638 (1988).

Clark-Lewis, et al., "Structure-Activity Relationships of Interleukin-8 Determined Using Chemically Synthesized Analogs," *J. Biol. Chem.*, 266(34):23128-23134 (Dec. 5, 1991).

Danoff, et al., "Cloning, Geonomic Organization, and Chromosomal Localization of the Scya5 Gene Encoding the Murine Chemokine RANTES," *J. Immunology*, 152:1182-1189 (1994).

Devi et al., "Biologic Activities of the beta-chemokine TCA3 on neutrophils and macrophages," *J. Immunol.* 154(10):5376-83 (1995).

Dunlop, et al., "Demonstration of Stem Cell Inhibition and Myeloprotective Effects of SCI/rhMIP1 α In Vivo," *Blood*, 79(9):2221-2225 (May 1, 1992).

Elstad, et al., "Synthesis and Release of Platelet-Activating Factor by Stimulated Human Mononuclear Phagocytes," *J. Immunology*, 140(5):1618-1624 (Mar. 1, 1988).

Fowlkes et al., "Multipurpose Vectors for Peptide Expression on the M13 Viral Surface," *BioTechniques*, 13(3):422-427 (1992).

Gao, et al., "Structure and Functional Expression of the Human Macrophage Inflammatory Protein 1α/Rantes Receptor," *J. Exp. Med.*, 177:1421-1427 (May, 1993).

Gerard, et al., "Human Chemotaxis Receptor Genes Cluster at 19q13.3-13.4. Characterization of the Human C5a Receptor Gene," *Biochemistry*, 32:1243-1250 (1993).

Gray, "Inflammatory Bowel Disease," in *Scientific American Medicine*, Dale & Federman (Eds.), New York: Scientific American, Inc., vol. 1, Chapter 4, Part IV, pp. 10-16 (1991).

Harada, et al., "Essential involvement of interleukin-8 (IL-8) in acute inflammation," *J. Leukocyte Biology*, 56:559-564 (Nov. 1994).

Holmes et al., "Structure and Functional Expression of a Human Interleukin-8 Receptor," *Science*, 253:1278-80 (Sep. 13, 1991).

Horuk, et al., "Purification, Receptor Binding Analysis, and Biological Characterization of Human Melanoma Growth Stimulating Activity (MGSA)," *J. Biol. Chem.*, 268(1):541-546 (Jan. 5, 1993).

(List continued on next page.)

Primary Examiner—Frank C. Eisenschenk
Attorney, Agent, or Firm—Marshall, O'Toole, Gerstein, Murray & Borun

[57] ABSTRACT

The present invention provides purified and isolated polynucleotide sequences encoding a novel human macrophage-derived C—C chemokine designated MDC. Also provided are materials and methods for the recombinant production of the chemokine, and purified and isolated chemokine protein.

10 Claims, 1 Drawing Sheet

OTHER PUBLICATIONS

Kelvin, et al., "Chemokines and Serpentines: The Molecular Biology of Chemokine Receptors," J. Leukocyte Biology, 54:604–612 (Dec., 1993).

Kuna, et al., "Rantes, A Monocyte and T Lymphocyte Chemotatic Cytokine Releases Histamine From Human Basophils," J. Immunology, 149(2):636–642 (Jul. 15, 1992).

Kurjan, et al., "Structure of a Yeast Pheromone Gene (MFα): A Putative–α–Factor Precursor Contains Four Tandem Copies of Mature α–Factor," Cell, 30:933–943 (Oct., 1992).

Laning, et al., "Inhibition of In Vivo Tumor Growth by the β Chemokine, TCA3," J. Immunology, 153:4625–4635 (1994).

Luo, et al., "Biologic Activities of the Murine β–Chemokine TCA3," J. Immunology, 153:4616–4624 (1994).

Matsushima, et al., "Purification and Characterization of a Novel Monocyte Chemotactic and Activating Factor Produced by a Human Myelomonocytic Cell Line," J. Exp. Med., 169:1485–1490 (Apr. 1989).

Maze, et al., "Myelosuppressive Effects in Vivo of Purified Recombinant Murine Macrophage Inflammatory Protein–1α," J. Immunology, 149(3):1004–1009 (Aug. 1, 1992).

Meurer, et al., "Formation of Eosinophilic and Monocytic Intradermal Inflammatory Sites in the Dog by Injection of Human RANTES but not Human Monocyte Chemoattractant Protein 1, Human Macrophage Inflammatory Protein 1α, or Human Interleukin 8," J. Exp. Med. 178:1913–1921 (Dec., 1993).

Miller, et al., "A Novel Polypeptide Secreted By Activated Human T Lymphocytes," J. Immunology, 143(9):2907–2916 (Nov. 1, 1989).

Murphy, et al., "Cloning of Complementary DNA Encoding a Functional Human Interleukin–8 Receptor," Science, 253:1280–83 (Sep. 13, 1991).

Nakao, et al., "Structures of Human Genes Coding for Cytokine LD78 and Their Expression," Molecular and Cellular Biology, 10(7):3646–3658 (Jul., 1990).

Neote et al., "Molecular Cloning, Functional Expression, and Signaling Characteristics of a C–C Chemokine Receptor," Cell, 72:415–425 (Feb. 12, 1993).

Perussia, et al., "Terminal Differentiation Surface Antigens of Myelomonocytic Cells are Expressed in Human Promyelocytic Leukemia Cells (HL60) Treated with Chemical Inducers," Blood, 58(4):836–843 (Oct., 1981).

Picker, et al., "Physiological and Molecular Mechanisms of Lymphocyte Homing," Annu. Rev. Immunol., 10:561–91 (1992).

Price, et al., "Expression, purification and characterization of recombinant murine granulocyte–macrophage colony-–stimulating factor and bovine interleukin–2 from yeast," Gene, 55:287–293 (1987).

Rose, et al., "Propagation and Expression of Cloned Genes in Yeast: 2–μm Circle–Based Vectors," Methods in Enzymology, 185:234–279 (1990).

Sambrook et al., Molecular Cloning: A Laboratory Manual. Cold Spring Harbor, New York: Cold Spring Harbor Laboratory (1989), pp. 6.1–6.35, 1.74–1.84, 1.90–1.104.

Sarris, et al., "Human Interferon–inducible Protein 10: Expressed and Purification of recombinant Protein Demonstrate Inhibition of Early Human Hematopoietic Progenitors," J. Exp. Med., 178:1127–1132 (Sep., 1993).

Schall, et al., "A Human T Cell–Specific Molecule is a Member of a New Gene Family," J. Immunology, 141(3):1018–1025 (Aug. 1, 1988).

Springer, "Traffic Signals for Lymphocyte Recirculation and Leukocyte Emigration: The Multistep Paradigm," Cell, 76:301–314 (Jan. 28, 1994).

Stafforini, et al., "Human Macrophages Secrete Platelet–activating Factor Acetylhydrolase," J. Biol. Chem., 265(17):9682–9687 (Jun. 15, 1990).

Stearns, et al., "Manipulating Yeast Genome Using Plasmid Vectors," Methods in Enzymology, 185:280–297 (1990).

Taub, et al., "Chemokines, inflammation and the immune system," Therapeutic Immunology, 1:229–246 (1994).

Tjoelker, et al., "Anti–inflammatory Properties of a Platelet–Activating Factor Aceytlhydrolase," Nature 374:549–553 (Apr. 6, 1995).

Van Damme, et al., "Structural and Functional Identification of Two Human, Tumor–derived Monocyte Chemotactic Proteins (MCP–2 and MCP–3) Belonging to the Chemokine Family," J. Exp. Med., 176:59–65 (Jul., 1992).

Von Heijne, et al., "A New Method For Predicting Signal Sequence Cleavage Sites", Nucleic Acids Research, 14(11):4683–4690 (1986).

Weber, et al., "Monocyte Chemotactic Protein MCP–2 Activates Human Basophil and Eosinophil Leukocytes Similar to MCP–3," J. Immunology, 154:4166–4172 (1995).

Wilson, et al., "Expression and Characterization of TCA3: A Murine Inflammatory Protein," J. Immunology, 145(8):2745–2750 (Oct. 15, 1990).

Peri et al., J. Immunol. Methods, 174:249, 1994.

Yoshimura et al., J. Immunol., 147:2229, 1991.

ALIGNMENT OF MDC to C-C CHEMOKINES

```
            Leader                              /    Mature

Hu MDC       MARLQTALLV VLVLLAVALQ ATEA    GPYGAN MEDSVCCRDY VRYRLPLRVV   50
Hu MCP-3     M-KASAALLC LLLTAAAFSP QGLA    QPVGIN -TSTTCCYRF INKKIPKQRL   48
Hu MCP-1     M-KVSAALLC LLLIAATFIP QGLA    QPDAIN -APVTCCYNF TNRKISVQRL   48
Hu MCP-2                                   QPD-SV SIPITCCFNV INRKIPIQRL   26
Hu RANTES    M-KVSAAALA VILIATALCA PASA    SPY-SS -DTTPCCFAY IARPLPRAHI   47
Hu MIP-1β    M-KLCVTVLS LLMLVAAFCS PALS    APM-GS DPPTACCFSY T-REASSNFV   47
Hu MIP-1α    M-QVSTAALA VLLCTMALCN QF-S    ASL-AA DTPTACCFSY TSRQIPQNFI   47
Hu I-309     MQIITTALVC LLL-AGMWPE DVDS    KS--MQ VPFSRCCFSF AEQEIPLRAI   47

Hu MDC       KH-FYWTSDS CPRPGVVLLT FRDKEICADP RVPWVKMILN KLSQ             93
Hu MCP-3     ESYRRTTSSH CPREAVIFKT KLDKEICADP TQKWVQDFMK HLDKKTQTPKL      99
Hu MCP-1     ASYRRITSSK CPKEAVIFKT IVAKEICADP KQKWVQDSMD HLDKQTQTPKT      99
Hu MCP-2     ESYTRITNIQ CPKEAVIFKT KRGKEVCADP KERWVRDSMK HLDQIFQNLKP      76
Hu RANTES    KEYFY-TSGK CSNPAVVFVT RKNRQVCANP EKKWVREYIN SLEMS            91
Hu MIP-1β    VDY-YETSSL CSQPAVVFQT KRSKQVCADP SESWVQEYVY DLELN            91
Hu MIP-1α    ADYF-ETSSQ CSKPGVIFLT KRSRQVCADP SEEWVQKYVS DLELSA           92
Hu I-309     LCY-RNTSSI CSNEGLIFKL KRGKEACALD TVGWVQRHRK MLRHCPSKRK       96
```

Fig. 1

MACROPHAGE DERIVED CHEMOKINE

FIELD OF THE INVENTION

The present invention relates generally to chemokines and more particularly to purified and isolated polynucleotides encoding a novel human C—C chemokine, to purified and isolated chemokine protein encoded by the polynucleotides, and to materials and methods for the recombinant production of the novel chemokine protein.

BACKGROUND

Chemokines, also known as "intercrines" and "SIS cytokines", comprise a family of small secreted proteins (e.g., 70–100 amino acids and 8–10 kiloDaltons) which attract and activate leukocytes and thereby aid in the stimulation and regulation of the immune system. The name "chemokine" is derived from chemotactic cytokine, and refers to the ability of these proteins to stimulate chemotaxis of leukocytes. Indeed, chemokines may comprise the main attractants for inflammatory cells into pathological tissues. See generally, Baggiolini et al., *Advances in Immunology*, 55:97–179 (1994). While leukocytes comprise a rich source of chemokines, several chemokines are expressed in a multitude of tissues. Id., Table II.

Previously identified chemokines generally exhibit 20–70% amino acid identity to each other and contain four highly-conserved cysteine residues. Based on the relative position of the first two of these cysteine residues, chemokines have been further classified into two subfamilies. In the "C-X-C" or "α" subfamily, encoded by genes localized to human chromosome 4, the first two cysteines are separated by one amino acid. In the "C—C" or "β" subfamily, encoded by genes on human chromosome 17, the first two cysteines are adjacent. X-ray crystallography and NMR studies of several chemokines have indicated that, in each family, the first and third cysteines form a first disulfide bridge, and the second and fourth cysteines form a second disulfide bridge, strongly influencing the native conformation of the proteins. In humans alone, nearly ten distinct sequences have been described for each chemokine subfamily. Chemokines of both subfamilies have characteristic leader sequences of twenty to twenty-five amino acids.

The C-X-C chemokines, which include IL-8, GROα/β/γ, platelet basic protein, Platelet Factor 4 (PF4), IP-10, and others, share approximately 25% to 60% identity when any two amino acid sequences are compared (except for the GROα/β/γ members, which are 84–88% identical with each other). Most of the C-X-C chemokines (excluding IP-10 and Platelet Factor 4) share a common E-L-R tri-peptide motif upstream of the first two cysteine residues, and are potent stimulants of neutrophils, causing rapid shape change, chemotaxis, respiratory bursts, and degranulation. These effects are mediated by seven-transmembrane-domain rhodopsin-like G protein-coupled receptors; a receptor specific for IL-8 has been cloned by Holmes et al., *Science*, 253:1278–80 (1991), while a similar receptor (77% identity) which recognizes IL-8, GRO and NAP2 has been cloned by Murphy and Tiffany, *Science*, 253:1280–83 (1991). Progressive truncation of the N-terminal amino acid sequence of certain C-X-C chemokines, including IL-8, is associated with marked increases in activity.

The C—C chemokines, which include Macrophage Inflammatory Proteins MIP-1α and MIP-1β, Monocyte chemoattractant proteins 1, 2, and 3 (MCP-1/2/3), RANTES, I-309, and others, share 25% to 70% amino acid identity with each other. All of the C—C chemokines activate monocytes, causing calcium flux and chemotaxis. More selective effects are seen on lymphocytes, for example, T lymphocytes, which respond best to RANTES. Two seven-transmembrane-domain G protein-coupled receptors for C—C chemokines have been cloned to date: a C—C chemokine receptor-1 which recognizes MIP-1α and RANTES (Neote et al., *Cell*, 72:415–425 (1993)), while the other recognizes MCP-1 (Charo et al., *Proc. Nat. Acad. Sci.*, 91:2752–56 (1994)).

The roles of a number of chemokines, particularly IL-8, have been well documented in various pathological conditions. See generally Baggiolini et al., supra, Table VII. Psoriasis, for example, has been linked to over-production of IL-8, and several studies have observed high levels of IL-8 in the synovial fluid of inflamed joints of patients suffering from rheumatic diseases, osteoarthritis, and gout.

The role of C—C chemokines in pathological conditions has also been documented, albeit less comprehensively than the role of IL-8. For example, the concentration of MCP-1 is higher in the synovial fluid of patients suffering from rheumatoid arthritis than that of patients suffering from other arthritic diseases. The MCP-1 dependent influx of mononuclear phagocytes may be an important event in the development of idiopathic pulmonary fibrosis. The role of C—C chemokines in the recruitment of monocytes into atherosclerotic areas is currently of intense interest, with enhanced MCP-1 expression having been detected in macrophage-rich arterial wall areas but not in normal arterial tissue. Expression of MCP-1 in malignant cells has been shown to suppress the ability of such cells to form tumors in vivo. (See U.S. Pat. No. 5,179,078, incorporated herein by reference.) A need therefore exists for the identification and characterization of additional C—C chemokines, to further elucidate the role of this important family of molecules in pathological conditions, and to develop improved treatments for such conditions utilizing chemokine-derived products.

Chemokines of the C—C subfamily have been shown to possess utility in medical imaging, e.g., for imaging the site of infection, inflammation, and other sites having C—C chemokine receptor molecules. See, e.g., Kunkel et al., U.S. Pat. No. 5,413,778, incorporated herein by reference. Such methods involve chemical attachment of a labelling agent (e.g., a radioactive isotope) to the C—C chemokine using art recognized techniques (see, e.g., U.S. Pat. Nos. 4,965,392 and 5,037,630, incorporated herein by reference), administration of the labelled chemokine to a subject in a pharmaceutically acceptable carrier, allowing the labelled chemokine to accumulate at a target site, and imaging the labelled chemokine in vivo at the target site. A need in the art exists for additional new C—C chemokines to increase the available arsenal of medical imaging tools.

More generally, due to the importance of chemokines as mediators of chemotaxis and inflammation, a need exists for the identification and isolation of new members of the chemokine family to facilitate modulation of inflammatory and immune responses.

For example, substances that promote inflammation may promote the healing of wounds or the speed of recovery from conditions such as pneumonia, where inflammation is important to eradication of infection. Modulation of inflammation is similarly important in pathological conditions manifested by inflammation. Crohn's disease, manifested by chronic inflammation of all layers of the bowel, pain, and diarrhea, is one such pathological condition. The failure rate of drug therapy for Crohn's disease is relatively high, and the disease is often recurrent even in patients receiving surgical intervention. The identification, isolation, and characterization of novel chemokines facilitates modulation of inflammation.

Similarly, substances that induce an immune response may promote palliation or healing of any number of pathological conditions. Due to the important role of leukocytes (e.g., neutrophils and monocytes) in cell-mediated immune responses, and due to the established role of chemokines in leukocyte chemotaxis, a need exists for the identification and isolation of new chemokines to facilitate modulation of immune responses.

Additionally, the established correlation between chemokine expression and inflammatory conditions and disease states provides diagnostic and prognostic indications for the use of chemokines, as well as for antibody substances that are specifically immunoreactive with chemokines; a need exists for the identification and isolation of new chemokines to facilitate such diagnostic and prognostic indications.

For all of the aforementioned reasons, a need exists for recombinant methods of production of newly discovered chemokines, which methods facilitate clinical applications involving the chemokines and chemokine inhibitors.

SUMMARY OF THE INVENTION

The present invention provides novel purified and isolated polynucleotides and polypeptides that fulfill one or more of the needs outlined above.

For example, the invention provides purified and isolated polynucleotides (i.e., DNA and RNA, both sense and antisense strands) encoding a novel human chemokine of the C—C subfamily, herein designated "Macrophage Derived Chemokine" or "MDC". Preferred DNA sequences of the invention include genomic and cDNA sequences and chemically synthesized DNA sequences.

The nucleotide sequence of a cDNA, designated MDC cDNA, encoding this chemokine, is set forth in SEQ ID NO: 1, which sequence includes 5' and 3' non-coding sequences. A preferred DNA of the present invention comprises nucleotides 20 to 298 of SEQ ID NO. 1, which nucleotides comprise the MDC coding sequence.

The MDC protein comprises a putative twenty-four amino acid signal sequence at its amino terminus. A preferred DNA of the present invention comprises nucleotides 92 to 298 of SEQ ID NO. 1, which nucleotides comprise the putative coding sequence of the mature (secreted) MDC protein, without the signal sequence.

The amino acid sequence of chemokine MDC is set forth in SEQ ID NO: 2. Preferred polynucleotides of the present invention include, in addition to those polynucleotides described above, polynucleotides that encode the amino acid sequence set forth in SEQ ID NO:2, and that differ from the polynucleotides described in the preceding paragraphs only due to the well-known degeneracy of the genetic code.

Similarly, since amino acids 1–24 of SEQ ID NO: 2 comprise a putative signal peptide that is cleaved to yield the mature MDC chemokine, preferred polynucleotides include those which encode amino acids 25 to 93 of SEQ ID NO: 2. Thus, a preferred polynucleotide is a purified polynucleotide encoding a polypeptide having an amino acid sequence comprising amino acids 25–93 of SEQ ID NO: 2.

Among the uses for the polynucleotides of the present invention is the use as a hybridization probe, to identify and isolate genomic DNA encoding human MDC, which gene is likely to have a three exon/two intron structure characteristic of C—C chemokines genes. (See Baggiolini et al., supra); to identify and isolate non-human proteins homologous to MDC; to identify human and non-human chemokines having similarity to MDC; and to identify those cells which express MDC and the conditions under which this protein is expressed.

In another aspect, the invention includes plasmid and viral DNA vectors incorporating DNAs of the invention, including any of the DNAs described above. Preferred vectors include expression vectors in which the incorporated MDC-encoding cDNA is operatively linked to an endogenous or heterologous expression control sequence. Such expression vectors may further include polypeptide-encoding DNA sequences operably linked to the MDC-encoding DNA sequences, which vectors may be expressed to yield a fusion protein comprising the MDC polypeptide of interest.

In another aspect, the invention includes a prokaryotic or eukaryotic host cell stably transfected or transformed with a DNA or vector of the present invention. In preferred host cells, the MDC polypeptide encoded by the DNA or vector of the invention is expressed. The DNAs, vectors, and host cells of the present invention are useful, e.g., in methods for the recombinant production of large quantities of MDC polypeptides of the present invention. Such methods are themselves aspects of the invention. For example, the invention includes a method for producing MDC wherein a host cell of the invention is grown in a suitable nutrient medium and MDC protein is isolated from the cell or the medium.

In yet another aspect, the invention includes purified and isolated MDC polypeptides. A preferred peptide is a purified chemokine polypeptide having an amino acid sequence comprising amino acids 25 to 93 of SEQ ID NO: 2. The polypeptides of the present invention may be purified from natural sources, but are preferably produced by recombinant procedures, using the DNAs, vectors, and/or host cells of the present invention, or are chemically synthesized. Purified polypeptides of the invention may be glycosylated or non-glyclosylated, water soluble or insoluble, oxidized, reduced, etc., depending on the host cell selected, recombinant production method, isolation method, processing, storage buffer, and the like.

Moreover, an aspect of the invention includes MDC polypeptide analogs wherein one or more amino acid residues is added, deleted, or replaced from the MDC polypeptides of the present invention, which analogs retain one or more of the biological activities characteristic of the C—C chemokines. N-terminal deletion analogs of MDC are specifically contemplated.

In a related aspect, the invention includes polypeptide analogs wherein one or more amino acid residues is added, deleted, or replaced from the MDC polypeptides of the present invention, which analogs lack the biological activities of C—C chemokines, but which are capable of competitively or non-competitively inhibiting the binding of MDC polypeptides with a C—C chemokine receptor. Such polypeptides are useful, e.g., for modulating the biological activity of endogenous MDC in a host, as well as useful for medical imaging methods described above.

In another aspect, the invention includes antibody substances (e.g., monoclonal and polyclonal antibodies, single chain antibodies, chimeric or humanized antibodies, and the like) which are immunoreactive with MDC to polypeptides and polypeptide analogs of the invention. Such antibodies are useful, e.g., for purifying polypeptides of the present invention, for quantitative measurement of endogenous MDC in a host, e.g., using well-known ELISA techniques, and for modulating binding of MDC to its receptor(s). The invention further includes hybridoma cells lines that produce antibody substances of the invention.

Recombinant MDC polypeptides and polypeptide analogs of the invention may be utilized in a like manner to antibodies in binding reactions, to identify cells expressing receptor(s) of MDC and in standard expression cloning techniques to isolate polynucleotides encoding the receptor (s). Such MDC polypeptides, MDC polypeptide analogs, and MDC receptor polypeptides are useful for modulation of MDC chemokine activity, and for identification of polypeptide and chemical (e.g., small molecule) MDC agonists and antagonists.

The foregoing aspects and numerous additional aspects will be apparent from the drawing and detailed description which follow.

BRIEF DESCRIPTION OF THE DRAWING

FIG. 1 is a comparison of the amino acid sequence of human MDC (SEQ ID NO: 2) with the amino acid sequences of other, previously characterized human C—C chemokines: MCP-3 (SEQ ID NO: 18) [Van Damme et al., J. Exp. Med., 176:59 (1992)]; MCP-1 (SEQ ID NO. 19) [Matsushima et al., J. Exp. Med., 169:1485 (1989)]; MCP-2 (SEQ ID NO: 20) (mature form) [Van Damme et al., supra; Chang et al., Int. Immunol., 1:388 (1989)]; RANTES (SEQ ID NO: 21) [Schall et al., J. Immunol., 141:1018 (1988)]; MIP-1β (SEQ ID NO: 22) [Brown et al., J. Immunol., 142:679 (1989)]; MIP-1α (SEQ ID NO: 23) [Nakao et al., Mol. Cell Biol., 10:3646 (1990)]; and I-309 (SEQ ID NO: 24) [Miller et al., J. Immunol., 143:2907 (1989)]. A slash "/" marks the site at which putative signal peptides are cleaved. Dashes are inserted to optimize alignment of the sequences.

DETAILED DESCRIPTION

The present invention is illustrated by the following examples related to a human cDNA, designated MDC cDNA, encoding a novel C—C chemokine designated MDC (for "macrophage-derived chemokine"). More particularly, Example 1 describes the isolation of a partial MDC cDNA from a human macrophage cDNA library. Example 2 describes the isolation of additional cDNAs from the cDNA library using the cDNA from Example 1 as a probe, one of these additional cDNAs containing the entire MDC coding sequence. Additionally, Example 2 presents a composite MDC cDNA nucleotide sequence and presents a characterization of the deduced amino acid sequence of the chemokine (MDC) encoded thereby. In Example 3, experiments are described which reveal the level of MDC gene expression in various human tissues. Example 4 describes more particularly the expression of the MDC gene during monocyte maturation into macrophages and during inducement of HL60 cell differentiation to a macrophage-like cell type.

Since MDC gene expression was detected in thymus and spleen in Example 3, in situ hybridization studies were conducted to localize further the MDC gene expression in these tissues. Moreover, in situ hybridization revealed a correlation between elevated MDC gene expression in intestinal tissue and Crohn's disease. These in situ hybridization experiments are described in Example 5.

Example 6 describes the recombinant production of MDC in prokaryotic cells, as well as the purification of this protein. Example 7 describes the construction of an alternative DNA construct useful for expression of recombinant MDC protein, and describes the transformation of a bacterial host with this construct.

Remaining examples 8–18 are prospective examples relating to additional aspects of the invention. For instance, Example 8 provides an experimental protocol for expression of the DNA construct described in Example 7, and for purification of the resultant MDC protein. Examples 9 and 10 provide experimental protocols for the recombinant production of MDC in yeast and mammalian cells, respectively. Example 11 describes production of MDC by peptide synthesis.

Examples 12–17 provide protocols for the determination of MDC biological activities. For instance, Example 12 provides an assay of MDC effects upon Basophils, Mast Cells, and Eosinophils. Example 13 describes assays of chemoattractant and cell-activation properties of MDC on monocytes/macrophages and neutrophils.

Examples 14–17 provide protocols for the determination of MDC biological activities in vivo. Example 14 provides an MDC tumor growth-inhibition assay. Examples 15 and 16 provide protocols for assaying MDC activity via intraperitoneal and subcutaneous injection, respectively. Example 17 provides protocols for determining the myelosuppressive activity of MDC.

Finally, Example 18 provides a protocol for generating monoclonal antibodies that are specifically immunoreactive with MDC.

EXAMPLE 1

Isolation of a Partial C—C Chemokine cDNA

A partial cDNA for a new C—C chemokine was isolated as follows. Poly A$^+$ RNA was harvested from peripheral blood monocyte-derived macrophages. Double-stranded, blunt-ended cDNA was generated using the Invitrogen Copy Kit (San Diego, Calif.) and BstXI adapters were ligated to the cDNA prior to insertion into the mammalian expression vector, pRc/CMV (Invitrogen) [See, Tjoelker et al., Nature, 374:549–552 (1995)]. E. coli XL1-Blue bacteria (Stratagene, La Jolla, Calif.) were transformed via electroporation with the plasmid cDNA library and plated onto 986 plates containing 100 µg/ml carbenicillin (approximately 3000 transformants per plate). After overnight growth at 37° C., the bacteria were scraped off of each plate to form 986 bacterial pools. Plasmid DNA was isolated from each of the 986 bacterial pools using the Magic Miniprep DNA Purification System (Promega, Madison, Wis.) according to the manufacturer's directions.

The purified plasmid DNA pools were used to isolate individual cDNA clones for further characterization, as follows: Plasmid DNA from individual pools was used to transform E. coli XL1-Blue cells, which were plated and grown overnight as described above. Individual transformants were randomly selected and grown overnight in 3 ml of LB media supplemented with carbenicillin for plasmid purification using the Wizard Miniprep Purification system (Promega) with the following alteration: 250 mg of diatomaceous earth (Sigma Chem. Co., St. Louis, Mo.) was added to the DNA binding resin provided by the manufacturer. Purified plasmid DNA was sequenced on a Model 373 automated sequencer (Applied Biosystems, Foster City, Calif.) using primer JHSP6:

5' GACACTATAGAATAGGGC 3' (SEQ ID NO: 3).

This primer hybridizes to plasmid vector pRc/CMV adjacent to the cloning site.

The nucleotide and deduced amino acid sequences of individual cDNAs were compared to nucleotide and peptide sequence databases to determine which of the clones encoded proteins with similarity to known inflammatory mediators. Sequence comparisons were performed on Dec. 14, 1994, by the BLAST Network Service of the National Center for Biotechnology Information (e-mail: "blast@ncbi.nlm.nih.gov"), using the alignment algorithm of Altschul et al., *J. Mol. Biol.*, 215:403–410 (1990). The sequence analysis revealed that a portion of one of the isolated macrophage cDNA clones, designated pMP390, contained a gene sequence having approximately 60–70% identity with previously-identified chemokine genes, including the human MCP-3 gene and rat MIP-1β gene.

The 2.85 kb cDNA insert of pMP390 was subcloned into the vector pBluescript SK⁻ (Stratagene, La Jolla, Calif.) to facilitate complete sequencing. Nested deletions beginning from the poly-A tail were created by digestion, using Promega's Erase-a-Base System (Madison, Wis.). The deletion plasmids were recircularized, cloned in *E. coli*, purified, and sequenced using the M13, T3.1, and T7.1 primers depicted below:

M13: 5' GTAAAACGACGGCCAGT 3' (SEQ ID NO: 4)

T3.1: 5' AATTAACCCTCACTAAAGGG 3' (SEQ ID NO: 5)

T7.1: 5' GTAATACGACTCACTATAGGGC 3' (SEQ ID NO: 6)

The complete sequence of this pMP390 cDNA corresponds to nucleotides 73 to 2923 of SEQ ID NO: 1 (and to deduced amino acids 19–93 of SEQ ID NO 2). The sequence that was originally compared to database sequences corresponds to nucleotides 73 to 610 of SEQ ID NO: 1.

EXAMPLE 2

Isolation of Additional cDNA Clones Having the Complete MDC Coding Sequence Using the pMP390 cDNA clone isolated in Example 1, additional cDNA clones were isolated from the same human macrophage cDNA library, these additional cDNAs containing additional 5' sequence and encoding the complete amino acid sequence of a macrophage derived chemokine.

First, forty of the 986 plasmid DNA pools derived from the macrophage cDNA library (Example 1) were screened by PCR to identify pools containing additional cDNA clones of interest. From the pMP390 cDNA sequence obtained in Example 1, synthetic oligonucleotide PCR primers 390-1F (deposited as SEQ ID NO: 7) and 390-2R (SEQ ID NO: 8) were constructed to amplify a 211 base pair sequence of the chemokine gene partially encoded by pMP390:

390-1F: 5' TCTATCTAGAGGCCCCTACGGCGCCAA-CATGGAAG 3'

390-2R: 5' CACCGGATCCTCATTGGCTCAGCTTATTGAGAA 3'

Primer 390-1F corresponds to nucleotides 91–116 of SEQ ID NO: 1, preceded by the recognition site for the restriction endonucleose Xba I and 4 additional bases to facilitate cleavage by the enzyme; primer 390-2R is complementary to nucleotides 301–279 of SEQ ID NO: 1, fused to the recognition site for the enzyme BamH I, which is flanked by 4 additional bases. The Xba I and BamH I sites were added to facilitate cloning of the resultant fragment.

The 50 ul PCR reaction mixture for each selected plasmid pool contained 0.2 ug of plasmid DNA; 1.5 mM MgCl₂; 50 mM KCl; 10 mM Tris, pH 8.4; 0.2 mM each dNTP; 10 ug/ml each primer; and 0.5 ul Taq polymerase (5 U/ul) (Boehringer Mannheim Biochemicals (BMB), Indianapolis, Ind.). The reactions were incubated for 4 minutes at 94° C., followed by 30 cycles of denaturation for 15 seconds at 94° C., annealing for 15 seconds at 60° C., and extension for 30 seconds at 72° C.

The PCR reaction products were electrophoresed through 2% agarose gels (Life Technologies, Inc., Gaithersburg, Md.) in 0.5X TBE buffer [Sambrook et al., *Molecular Cloning: a Laboratory Manual*. Cold Spring Harbor, N.Y.: Cold Spring Harbor Laboratory (1987)], and visualized with Ethidium Bromide. Of the forty plasmid pools screened, six produced an intense band corresponding to the expected 230 base pair PCR fragment (which includes 211 bp of chemokine gene sequence flanked by the Xba I and BamH I restriction sites) suggesting the presence of one or more plasmids containing gene sequences related to pMP390.

To isolate such related clones, aliquots from three of the six positive plasmid pools were electroporated into *E. coli* XL1-Blue cells, which were plated and grown overnight as described in Example 1. Colonies were transferred to nitrocellulose membranes and prepared for hybridization following standard protocols (Sambrook et al., supra).

A radiolabelled MDC probe for screening the filters was prepared as follows: the 2.85 kb DNA fragment containing the MDC cDNA was excised from pMP390 by restriction enzyme digestion, purified by agarose gel electrophoresis in TAE Buffer (Sambrook, et al., supra), electroeluted, extracted with phenol and chloroform, and preciptated with ethanol. The purified fragment (250 ng) was labelled using the Random Primed DNA Labelling Kit (BMB) according the manufacturer's recommendations. The labelled probe was purified by passage through a G-50 Quick Spin column (BMB).

The filters were incubated at 42° C. for 16 hours with $5 \times 10^7$ counts per minute (cpm) of the probe, in 40–50 ml of a solution containing 50% formamide, 5X Denhardt's solution, 5X SSC (1X SSC is 0.15M NaCl, 15 mM sodium citrate), 50 mM sodium phosphate, pH 6.5, and 0.1 mg/ml sheared salmon sperm DNA (Sigma, St. Louis, Mo.). Following hybridization, the filters were washed 3 times in 0.2X SSC and 0.2% SDS at 55° C., for 30 minutes. To visualize hybridization, the washed filters were exposed overnight at −80° C. on Kodak (Rochester, N.Y.) XAR-5 autoradiographic film with Lightning Plus intensifying screens (DuPont, Del.).

PCR was used to screen 50 of the hybridizing bacterial colonies. Fifty PCR reactions containing primers 390-1F and 390-2R were set up as described above, using bacteria from the fifty colonies in place of template DNA. Initially, the reactions were denatured at 94° C. for 8 minutes. Thereafter, 35 cycles of amplification were carried out as described above. A single colony produced the expected 230 basepair product; the plasmid contained in this clone was designated pMP390-12.

Additional MDC cDNA's of interest were identified by colony hybridization using a probe specific for the 5' end of the pMP390 insert. This probe was prepared as follows: a DNA fragment containing 211 bases of the coding region of the pMP390 cDNA (nucleotides 91–298 of SEQ. ID NO: 1) and 163 bases of the adjacent 3' non-coding region was generated by PCR as described above, using 60 ng of the pMP390 cDNA clone as template and synthetic oligonucleotides 390-1F (SEQ ID NO: 7) and 390-4R (SEQ ID NO: 9) as primers.

390-4R: 5' AATGGATCCACAGCACGGAGGTGACCAAG 3'

Primer 390-4R contains a BamH I restriction site followed by sequence complementary to nucleotides 461 to 442 of SEQ ID NO: 1.

The PCR product was purified by electrophoresis as described above, and fifty ng of the purified fragment was labelled with the Random Primed DNA Labelling Kit (BMB) and purified by passage through a G-50 Quick Spin column (BMB). Filters were probed with this fragment as described above, and washed three times in 0.4 X SSC and 0.2% SDS at 48° C. for 30 minutes. Autoradiography was carried out as described above. Five hybridizing colonies were detected, designated MP390A, MP390B, MP390C, MP390D, and MP390E.

These five colonies and a colony transformed with pMP390-12 were isolated and grown for plasmid purification, using the Wizard Miniprep DNA Purification System (Promega, Madison, Wis.) with the addition of diatomaceous earth as described in Example 1. Plasmid DNA was sequenced on an Applied Biosystems Model 373 automated sequencer, using synthetic primer 390-3R (SEQ ID NO: 10):

390-3R: 5' AGTCAAGCTTAGGGCACTCTGGGATCGGCAC 3'.

Primer 390-3R is complementary to bases 266–246 of SEQ ID NO: 1, and contains a Hind III restriction endonuclease site and four additional base pairs at its 5' terminus. The primer was designed to anneal upstream of primer 390-2R and downstream of nucleotide 216 of SEQ ID NO: 1, the site at which an intron is predicted in the genomic DNA encoding the chemokine of the present invention [See Danoff et al., *J. Immunology*, 152:1182–1189 (1994)].

Of the six clones, clones pMP390-12 and pMP390B contained the largest additional 5' coding sequence, each extending an additional 72 nucleotides upstream of the sequence previously obtained from the cDNA clone pMP390. A composite DNA sequence, herein designated MDC cDNA, was generated by alignment of the pMP390 and pMP390-12 cDNA sequences. This 2923 base pair composite cDNA sequence, and the deduced amino acid sequence of the chemokine MDC, are set forth in SEQ ID NOs: 1 and 2, respectively.

Manual comparison of the deduced MDC amino acid sequence with sequences of known chemokines indicates that the MDC cDNA sequence encodes a novel C—C chemokine ninety-three amino acids in length, sharing 28–34% amino acid identity with other C—C chemokines (FIG. 1 and Table 1).

Importantly, the four cysteine residues characteristic of the chemokines are conserved in MDC. Five additional residues also are completely conserved in the eight sequences presented in FIG. 1.

The first 24 amino acids of the MDC sequence are predominantly hydrophobic and are consistent with von Heijne's rules [Nucleic Acids Res., 14: 4683–90 (1986)] governing signal cleavage. These features and the polypeptide comparison in FIG. 1 collectively suggest that the MDC cDNA encodes a twenty-four amino acid signal peptide that is cleaved to produce a mature form of MDC beginning with the glycine residue at position 25 of SEQ ID NO: 2. The MDC composite cDNA sequence shown in SEQ ID NO: 1 extends nineteen nucleotides upstream of the predicted initiating methionine codon, and 2.6 kb downstream of the termination codon.

EXAMPLE 3

Determination of MDC Gene Expression in Human Tissues

Northern blot analyses were conducted to determine the tissues in which the MDC gene is expressed.

The radiolabelled pMP390 5' fragment described in Example 2 (which corresponds to the region of the MDC cDNA encoding the putative mature form of MDC plus 163 bases of the adjacent 3' noncoding region) was used to probe Multiple Tissue Northern blots (Clontech, Palo Alto, Calif.) containing RNA from various human tissues. The probe was denatured by boiling prior to use, and the hybridizations were conducted according to the manufacturer's specifications. Autoradiographs were exposed 5 days at −80° C. with 2 intensifying screens.

The greatest MDC gene expression was observed in the thymus, with much weaker expression detectable in spleen and lung tissues. Expression of MDC in tissue from the small intestine was at even lower levels, and no expression was detected in brain, colon, heart, kidney, liver, ovary, pancreas, placenta, prostate, skeletal muscle, testis, or peripheral blood leukocytes.

EXAMPLE 4

MDC Gene Expression During Macrophage Maturation

Because the cDNAs encoding MDC were isolated from a human macrophage cDNA library, MDC gene expression during differentiation of monocytes into macrophages was examined. Human monocytes from a single donor were cultured on a series of tissue culture plates, and cells from one plate were harvested after 0, 2, 4 or 6 days. See generally Elstad et al., *J. Immunol.* 140:1618–1624; Tjoelker et al.,

TABLE 1

Percent Identity Among Amino Acid Sequences of MDC and Previously Identified C—C Chemokines

| | MDC | MCP-1 | MCP-2 | MCP-3 | RANTES | MIP-1α | MIP-1β | I-309 |
|---|---|---|---|---|---|---|---|---|
| MDC | | 29% | 28% | 33% | 34% | 29% | 33% | 32% |
| MCP-1 | 29% | | 62% | 72% | 34% | 38% | 34% | 33% |
| MCP-2 | 28% | 62% | | 59% | 30% | 36% | 33% | 34% |
| MCP-3 | 33% | 72% | 59% | | 34% | 35% | 35% | 37% |
| RANTES | 34% | 34% | 30% | 34% | | 50% | 44% | 22% |
| MIP-1α | 29% | 38% | 36% | 35% | 50% | | 55% | 35% |
| MIP-1β | 33% | 34% | 33% | 35% | 44% | 55% | | 31% |
| I-309 | 32% | 33% | 34% | 37% | 22% | 35% | 31% | | supra. Under these conditions, the monocytes differentiated into macrophages by days 4–6 [Stafforini et al., *J. Biol. Chem.*, 265:9682–9687 (1990)].

A Northern blot of RNA (10 µg per lane) isolated from the cells harvested at each time point was prepared and probed, using the radiaolabelled pMP390 fragment as described above. No signal was detectable in RNA from freshly isolated monocytes, whereas a very strong signal was generated from cells that had differentiated into macrophages after six days of culture. Cells cultured for four days produced a much weaker signal, whereas the signal generated from cells cultured for two days could be seen only after prolonged exposure of the filter.

Further examination of MDC gene expression in macrophages was conducted by treating the human cell line HL60 with either 1% DMSO (Sigma Chemical Co., St. Louis, Mo.) or 50 ng/ml PMA (Sigma Chemical Co., St. Louis, Mo.). Treatment with DMSO induces differentiation of HL60 cells into a granulocytic cell type, whereas PMA induces their differentiation into a macrophage lineage [Perussia et al., *Blood*, 58:836–843 (1981)]. RNA was isolated from untreated cells and from cells treated for one or three days with DMSO or PMA, electrophoresed (10 µg/lane), and blotted. The Northern blot of the RNA was probed with the radiolabelled pMP390 5' fragment described in Example 3.

After three days of PMA treatment, the HL-60 cells clearly expressed MDC mRNA, although the level of expression was apparently less than that of macrophages after six days of culture (see above). No expression was seen after one day of treatment or in untreated cells. Further, no detectable expression of MDC was induced by treatment with DMSO for one or three days.

EXAMPLE 5

In situ Hybridization

Because MDC gene expression was detected in the thymus and spleen, in situ hybridization was carried out to localize the source of the message in these tissues. Further, in situ hybridization was used to correlate MDC gene expression to inflammation of intestinal tissue associated with Crohn's disease.

To generate radiolabelled in situ hybridization probes, a DNA fragment (nucleotides 91 to 301 of SEQ ID NO: 1) containing the MDC coding region was subcloned into the vector pBluescdpt SK⁻. T3 and T7 RNA polymerases (BMB) were used according to the manufacturer's directions to incorporate $^{35}$S-UTP into RNA transcripts complementary to each strand of the gene.

Normal human spleen, thymus, and colon tissue samples, as well as colon tissue samples from patients with Crohn's disease, were obtained from the National Disease Research Interchange (Philadelphia, Pa.). The tissue donors were as follows: normal thymus: nineteen year old male Caucasian, death due to motor vehicle accident, tissue removed at autopsy; normal spleen: 51 year old black male, death due to cerebral hemorrhage, tissue removed at autopsy; normal colon: black female, tissue removed during surgery: Crohn's colon #1: female, race not available, 46 years old, ulcerative colitis patient, tissue removed during surgery; Crohn's colon #2: eighteen year old male, race not available, Crohn's disease patient, tissue removed during surgery.

These tissues were prepared for in situ hybridization as follows. Tissue samples were imbedded in "OCT" compound (Miles, Inc., Elkhart, Ind.) and sectioned to a thickness of 6 microns using a cryostat 2800E (Leica). The tissue sections were adhered to slides coated with Vectabond (Vector Laboratories, Burlingame, Calif.), fixed in 4% paraformaldehyde for 20 min. at 4° C., dehydrated with ethanol, and denatured at 70° C. with 70% formamide and 2X SSC.

Hybridizations were performed by incubating the slides for 16 hours at 55° C. with the radiolabelled sense or anti-sense strand in an aqueous hybridization solution containing 50% formamide, 0.3M NaCl, 20 mM Tris pH 7.5, 10% dextran sulfate, 1X Denhardt's solution, 100 nM dithiothreitol, and 5 mM EDTA. After hybridization, the slides were incubated for one hour at room temperature in 4X SSC and 10 mM DTT. The slides were then washed at room temperature in 2X SSC; at 60° C. in 1X SSC; and finally at room temperature in 0.1X SSC. Specimens were dehydrated in ethanol and then coated with Kodak NTB2 photographic emulsion, air-dried for 2 hours, exposed for 11 days at 4° C., developed, and counterstained with hematoxylin/eosin.

Observed hybridization of the anti-sense strand indicated that the MDC gene was expressed in cells throughout the cortex of normal human thymus, with weak signal in the follicles. Expression of MDC in the thymus may indicate a T lymphocyte developmental role of MDC. Expression in normal human spleen was localized to cells of the red pulp, whereas little signal was detected in the white pulp.

Colon samples from patients with Crohn's disease exhibited hybridization in cells of the epithelium, lamina propria, Payer's patches, and smooth muscle. In contrast, normal human colon showed no hybridization above background. The observed pattern of MDC expression in the colons of Crohn's disease patients closely correlates with the expression of a macrophage-specific gene, Platelet Activating Factor Acetylhydrolase (PAF-AH) [Tjoelker et al., supra]. This result, together with the data presented in Example 4, suggest that macrophages express MDC cDNA in vivo during pathogenic inflammation. Moreover, the identification of MDC in Crohn's disease colon tissue samples suggest diagnostic relevance of MDC levels (e.g., in a patient's blood, stool sample, and/or intestinal lesions) to a patient's disease state or clinical prognosis.

EXAMPLE 6

Production of Recombinant MDC

To produce recombinant MDC protein, the sequence encoding the putative mature form of the protein was amplified by PCR and cloned into the vector pGEX-3X (Pharmacia, Piscataway, N.J.). The pGEX vector is designed to produce a fusion protein comprising glutathione-S-transferase (GST), encoded by the vector, and a protein encoded by a DNA fragment inserted into the vector's cloning site.

The standard PCR conditions described in Example 2 were again employed to amplify an MDC cDNA fragment using the primers 390-2R and 390-FX2 (SEQ ID NO: 11):

5'TATCGGATCCTGGTTCCGCGTGGC-
CCCTACGGCGCCAACATGGAA3'

Primer 390-FX2 contains a BamH I restriction site, followed by a sequence encoding a thrombin cleavage site [Chang et al., *Eur. J. Biochem.*, 151:217 (1985)] followed by bases 92–115 of SEQ ID NO: 1. The thrombin cleavage site is as follows: leucine-valine-proline-arginine-glycine-proline, in which glycine and proline are the first two residues of the predicted mature form of MDC. Treatment of the recombinant fusion protein with thrombin is expected to cleave the arginine-glycine bond of the fusion protein, releasing the predicted mature chemokine from the GST fusion.

The PCR product was purified by agarose gel electrophoresis, digested with BamH I endonuclease, and cloned into the BamH I site of pGEX-3X. This pGEX-3X/MDC construct was transformed into *E. coli* XL-1 Blue cells (Stratagene, La Jolla, Calif.), and individual transformants were isolated and grown. Plasmid DNA from individual transformants was purified and partially sequenced using an automated sequencer and primer GEX5 (SEQ ID NO: 12), which hybridizes to the pGEX-3X vector near the BAMH1 cloning site:

GEX5: 5' GAAATCCAGCAAGTATATAGCA 3'

The sequence obtained with this primer confirmed the presence of the desired MDC insert in the proper orientation.

Induction of the GST-MDC fusion protein was achieved by growing the transformed XL-1 Blue culture at 37° C. in LB medium (supplemented with carbenicillin) to an optical density at wavelength 600 nm of 0.4, followed by further incubation for 4 hours in the presence of 0.25 to 1.0 mM Isopropyl β-D-Thiogalactopyranoside (Sigma Chemical Co., St. Louis, Mo.).

The fusion protein, produced as an insoluble inclusion body in the bacteria, was purified as follows. Cells were harvested by centrifugation; washed in 0.15M NaCl, 10 mM Tris, pH 8, 1 mM EDTA; and treated with 0.1 mg/ml lysozyme (Sigma Chemical Co.) for 15 minutes at room temperature. The lysate was cleared by sonication, and cell debris was pelleted by centrifugation for 10 minutes at 12,000 X g. The fusion protein-containing pellet was resuspended in 50 mM Tris, pH 8, and 10 mM EDTA, layered over 50% glycerol, and centrifuged for 30 min. at 6000 X g. The pellet was resuspended in standard phosphate buffered saline solution (PBS) free of $Mg^{++}$ and $Ca^{++}$. The fusion protein, which remained insoluble, was approximately 80–90% of the protein mass and migrated in denaturing SDS-polyacrylamide gels with a relative molecular weight of 33 kD. The protein yield, as judged by Coomassie staining, was approximately 100 mg/l of *E. coli* culture.

The fusion protein was subjected to thrombin digestion to cleave the GST from the mature MDC protein. The digestion reaction (20–40 ug fusion protein, 20–30 units human thrombin (4000 U/mg (Sigma) in 0.5 ml PBS) was incubated 16–48 hrs. at room temperature and loaded on a denaturing SDS-PAGE gel to fractionate the reaction products. The gel was soaked in 0.4M KCl to visualize the protein bands, which migrated as fragments of approximately 26 kD and 7kD.

The identity of the 7 kD SDS-PAGE fragment was confirmed by partial amino acid sequence analysis. First, the protein was excised from the gel, electroeluted in 25 mM Tris base and 20 mM glycine, and collected onto a PVDF membrane in a ProSpin column (Applied Biosystems, Foster City, Calif.). Subjecting the sample to automated sequencing (Applied Biosystems Model 473A, Foster City, Calif.) yielded 15 residues of sequence information, which corresponded exactly to the expected N-terminus of the predicted mature form of MDC (SEQ ID NO: 2, amino acid residues 25 to 39).

EXAMPLE 7

Construction of a Bacterial MDC Expression Vector

The portion of the MDC cDNA encoding the predicted mature MDC protein was cloned into a plasmid containing the arabinose promoter and the pelB leader sequence [see Better et al., *Science*, 240:1041–43 (1988)].

More particularly, an MDC cDNA was amplified by PCR as described in Example 2, using approximately 0.1 μg of pMP390-12 as template and synthetic oligonucleotide primers 390-2R and 390-Pel (SEQ ID NO: 13):

390-Pel: 5' ATTGCCATGGCCGGCCCCTACGGCGC-CAACATGGAA 3'

Primer 390-Pel contains an Nco I restriction site, followed by two cytosine residues, followed by bases 92 to 115 of SEQ ID NO: 1.

The expected PCR product of 232 bp was purified by agarose gel electrophoresis, digested with Nco I and BamH I, and cloned along with a portion of the arabinose operon and pelB leader sequence (Better et al., supra) into the vector pUC19 (New England Biolabs, Beverly, Mass.). The resultant construct, designated pel390, encodes a fusion of the pelB leader (encoded by the vector) to the mature MDC protein. The sequence of this construct was confirmed by automated sequencing using the primers 390-2R and 390-Pel. The plasmid pel390 was transformed into *E. coli* strain MC1061 using standard procedures employing $CaCl_2$ incubation and heat shock treatment of the bacteria (Sambrook et al. supra.)

EXAMPLE 8

Production of Recombinant MDC in Bacteria

Following is an experimental protocol for expression of construct pel390 and purification of the recombinant MDC encoded thereby.

The *E. coli* transformed with pel390 are grown in LB medium supplemented with carbenicillin, and production of a pelB/MDC fusion is induced by growth for 16 hours in the presence of 0.5% arabinose. The pelB leader effects secretion of the mature MDC protein, the leader being cleaved during secretion [Better et al., supra].

The secreted recombinant MDC protein is purified from the bacterial culture media by, e.g., adapting methods previously described for the purification of recombinantly produced RANTES chemokine [Kuna et al., *J. Immunol.*, 149:636–642 (1992)], MGSA chemokine [Horuk et al., *J. Biol. Chem.* 268:541–46 (1993)], and IP-10 chemokine (expressed in insect cells) [Sarris et al., *J. Exp. Med.*, 178:1127–1132 (1993)].

EXAMPLE 9

Recombinant Production of MDC in Yeast

Following are protocols for the recombinant expression of MDC in yeast and for the purification of the recombinant MDC.

The coding region of the MDC cDNA is amplified from pMP390-12 by PCR, using as primers synthetic oligonucleotides containing the MDC cDNA sequences present in primers 390-1F and 390-2R. A DNA encoding the yeast pre-pro-alpha leader sequence is amplified from yeast genomic DNA in a PCR reaction using one primer containing bases 1–20 of the alpha mating factor gene and another primer complimentary to bases 255–235 of this gene [Kurjan and Herskowitz, *Cell*, 30:933–943 (1982)]. The pre-pro-alpha leader coding sequence and MDC coding sequence fragments are ligated into a plasmid containing the yeast alcohol dehydrogenase (ADH2) promoter, such that the promoter directs expression of a fusion protein consisting of the pre-pro-alpha factor fused to the mature MDC polypeptide. As taught by Rose and Broach, *Meth. Enz.* 185:234–279, D. Goeddel, ed., Academic Press, Inc., San Diego, Calif. (1990), the vector further includes an ADH2 transcription terminator downstream of the cloning site, the yeast "2-micron" replication origin, the yeast leu-2d gene, the yeast REP1 and REP2 genes, the *E. coli* beta-lactamase gene, and an *E. coli* origin of replication. The beta-lactamase and leu-2d genes provide for selection in bacteria and yeast, respectively. The leu-2d gene also facilitates increased copy number of the plasmid in yeast to induce higher levels of expression. The REP1 and REP2 genes encode proteins involved in regulation of the plasmid copy number.

The DNA construct described in the preceding paragraph is transformed into yeast cells using a known method, e.g., lithium acetate treatment [Stearns et al., *Meth. Enz.*, supra, pp. 280–297]. The ADH2 promoter is induced upon exhaustion of glucose in the growth media [Price et al., *Gene*, 55:287 (1987)]. The pre-pro-alpha sequence effects secretion of the fusion protein from the cells. Concomitantly, the yeast KEX2 protein cleaves the pre-pro sequence from the mature MDC chemokine [Bitter et. al., *Proc. Natl. Acad. Sci. USA*, 81:5330–5334 (1984)].

Alternatively, MDC is recombinantly expressed in yeast using a commercially available expression system, e.g., the Pichia Expression System (Invitrogen, San Diego, Calif.), following the manufacturer's instructions. This system also relies on the pre-pro-alpha sequence to direct secretion, but transcription of the insert is driven by the alcohol oxidase (AOX1) promoter upon induction by methanol.

The secreted MDC is purified from the yeast growth medium by, e.g., the methods used to purify MDC from bacterial and mammalian cell supernatants (see Examples 8 and 10).

EXAMPLE 10

Recombinant Production of MDC in Mammalian Cells

A truncated version of the MDC cDNA was synthesized by PCR as described in Example 2, using pMP390-12 as template and the synthetic oligonucleotides 390RcH and 390RcX as primers.

390RcH: 5'GACCAAGCTTGAGACATACAGG
ACAGAGCA          (SEQ ID NO: 14)

390RcX: 5'TGGATCTAGAAGTTGGCACAGG
CTTCTGG          (SEQ ID NO: 15)

Primer 390RcH contains a Hind III restriction site followed by bases 1 to 20 of SEQ ID NO: 1; primer 390RcX contains an Xba I restriction site followed by the sequence complimentary to bases 403 to 385 of SEQ ID NO: 1.

The expected 423 bp PCR product was purified by agarose gel electrophoresis and cloned into Hind III/Xba I-digested pRc/CMV (a vector which allows for direct expression in mammalian cells). The resulting plasmid, designated 390HXE, contained bases 1 to 403 of SEQ ID NO: 1. The sequence of the insert was confirmed by automated sequencing using the primers DC03 (SEQ ID NO: 16) and JHSP6.

DC03: 5' CGA AAT TAA TAC GAC TCA CT 3'

Primer DC03 anneals to the pRc/CMV vector sequence adjacent to the cloning site.

Another MDC cDNA construct was generated by PCR, using pMP390-12 as template and the primers 390RcH and 390mycRX (SEQ ID NO: 17).

390mycRX: 5' TGGATCTAGATCAATTCAAGTCCTCCTCGCT
GATCAGCTTCTGCTCTTGGCTCAGCTTATTGAGAAT 3'

Primer 390mycRX contains an Xba I restriction site, a sequence complementary to the sequence encoding a "myc" epitope [Fowlkes et al., *BioTechniques*, 13:422–427 (1992)], and a sequence complementary to bases 298 to 278 of SEQ ID NO: 1. This reaction amplified the expected 354 bp fragment containing bases 1 to 298 of SEQ ID NO: 1 fused to a "myc" epitope at the MDC carboxy-terminus. This epitope can be used to facilitate immunoprecipitation, affinity purification, and detection of the MDC-myc fusion protein by Western blotting. The fragment was cloned into pRc/CMV to generate the plasmid 390HmX. The sequence of the insert was confirmed by automated sequencing using the primer DC03.

Two transfection protocols were used to express the two MDC cDNA constructs described above: transient transfection into the human embryonic kidney cell line 293T and stable transfection into the mouse myeloma cell line NS0 (ECACC 85110503).

Transient transfection of 293T cells was carried out by the calcium phosphate precipitation protocol of Chen and Okayama, *BioTechniques*, 6:632–638 (1988) and *Mol. Cel. Biol.*, 87:2745–2752 (1987). Cells and supernatants were harvested four days after transfection. A Northern blot was prepared from 4 ug of total RNA from each cell lysate and probed with a radiolabelled MDC fragment prepared by PCR. The template for the labelling reaction was the PCR fragment previously generated by amplifying pMP390 with the primers 390-1F and 390-4R (see Example 2). Approximately 30 ng of this fragment was employed in a PCR reaction containing the following: 1.5 mM $MgCl_2$, 50 mM KCl, 10 mM Tris, pH 8.4, 0.2 mM dATP, 0.2 mM dTTP, 0.2 mM dGTP, 1 uM dCTP, 50 uCi $\alpha^{32}P$-dCTP (DuPont/New England Nuclear, Boston, Mass.), 2.5 U Taq polymerase, and 10 ug/ml each of primers 390-1F and 390-2R. The reaction was denatured by heating for 4 minutes at 94° C., followed by 15 cycles of amplification as described in Example 2. The probe was purified by passage over a G-25 Quick Spin column (BMB). Conditions for hybridization were described in Example 2. Filters were subsequently washed in 0.5 X SSC and 0.2% SDS at 42° C. for 30 minutes. Autoradiography was carried out at −80° C. with one intensifying screen for sixteen hours. The MDC DNA constructs were very highly expressed in the transfected cells and not detectable in the non-transfected cells.

For stable transfections, NS0 cells were grown to 80% confluency in D-MEM (Gibco), collected by centrifugation, and washed with PBS. Twenty ug of plasmid DNA was linearized with Sca I restriction endonuclease (BMB), added to the cells, and incubated on ice for 15 minutes in a 0.4 cm gap cuvette (BioRad, Hercules, Calif.). The cells were electroporated with two pulses of 3 microfarad at 1.5 kilovolts. Cells were diluted into 20 ml D-MEM, incubated at 37° C. in 5% $CO_2$ for 24 hours, and selected by plating into 96-well plates at various dilutions in D-MEM containing 800 ug/ml geneticin. Wells containing single drug-resistant colonies were expanded in selective media. Total RNA was analyzed by Northern blotting as described in the preceding paragraph. Message for MDC was seen only in transfected cell lines.

MDC is purified from mammalian culture supernatants by, e.g., adapting methods described for the purification of recombinant TCA3 chemokine [Wilson et al., *J. Immunol.*, 145:2745–2750 (1990)].

EXAMPLE 11

Production of MDC by Peptide Synthesis

MDC and MDC peptide analogs are prepared by chemical peptide synthesis using techniques that have been used successfully for the production of other chemokines such as IL-8, Clark-Lewis et al., *J. Biol Chem.*, 266:23128–34 (1991), and MCP-1. Such methods are advantageous because they are rapid, reliable for short sequences such as chemokines, and enable the selective introduction of novel, unnatural amino acids and other chemical modifications.

The chemoattractant and/or cell-activation properties of MDC on one or more types of cells involved in the inflammatory process, (e.g., T lymphocytes, monocytes, macrophages, basophils, eosinophils, neutrophils, mast cells, endothelial cells, epithelial cells or others) are assayed by art-recognized techniques that have been used for assaying such properties of numerous other chemokines. Native MDC or recombinant MDC purified and isolated as described in one or more of the preceding examples is assayed for activity as described in the following examples.

EXAMPLE 12

Assay of MDC Effects Upon Basophils, Mast Cells, and Eosinophils

The effect of MDC upon basophils, mast cells, and eosinophils is assayed, e.g., by methods described by Weber et al., *J. Immunol.*, 154:4166–4172 (1995) for the assay of MCP-1/2/3 activities. In these methods, changes in free cytosolic calcium and release of proinflammatory mediators (such as histamine and leukotriene) are measured. Blocking chemokine-mediated activation of these cell types has implications in the treatment of late-phase allergic reactions, in which secretion of proinflammatory mediators plays a significant role [Weber et al., supra].

EXAMPLE 13

Assay of Chemoattractant and Cell-Activation Properties of MDC Upon Human Monocytes/ Macrophages and Human Neutrophils The effects of MDC upon human monocytes/ macrophages or human neutrophils is evaluated, e.g., by methods described by Devi et al., *J. Immunol.*, 153:5376–5383 (1995) for evaluating murine TCA3-induced activation of neutrophils and macrophages. Indices of activation measured in such studies include increased adhesion to fibrinogen due to integrin activation, chemotaxis, induction of reactive nitrogen intermediates, respiratory burst (superoxide and hydrogen peroxide production), and exocytosis of lysozyme and elastase in the presence of cytochalasin B. As discussed by Devi et al., these activities correlate to several stages of the leukocyte response to inflammation. This leukocyte response, reviewed by Springer, *Cell*, 76:301–314 (1994), involves adherence of leukocytes to endothelial cells of blood vessels, migration through the endothelial layer, chemotaxis toward a source of chemokines, and site-specific release of inflammatory mediators. The involvement of MDC at any one of these stages provides an important target for clinical intervention, for modulating the inflammatory response.

In one art-recognized chemotaxis assay, a transmigration assay, leukocyte cells to be tested are radiolabelled by incubating for one hour at 37° C. in $^{51}$Cr (500 uCi/ml). After extensive washes, the cells are resuspended in Hank's balanced saline solution (Sigma Chemical Co.) plus 5% bovine serum albumin, 10 mM glucose, 0.8 mM $MgSO_4$, 1.2 mM $CaCl_2$, and then added quantitatively to the upper chamber of the transwells containing polycarbonate membranes, 8.0 um pore size (Costar, Cambridge, Mass.). MDC diluted in the same buffer is added to the lower chamber of the transwells at various concentrations. Transwell plates are incubated for 0.5–2.5 hours at 37° C. At the end of the assay, cells that have transmigrated through the membrane into the lower chamber are collected and counted in a Gamma scintillation counter.

EXAMPLE 14

MDC In Vivo Tumor Growth Inhibition Assay

Tumor growth-inhibition properties of MDC are assayed, e.g., by modifying the protocol described by Laning et al., *J. Immunol.*, 153:4625–4635 (1994) for assaying the tumor growth-inhibitory properties of murine TCA3. An MDC-encoding cDNA is transfected by electroporation into the myeloma-derived cell line J558 (American Type Culture Collection, Rockville, Md.). Transfectants are screened for MDC production by standard techniques such as ELISA (enzyme-linked immunoadsorbant assay) using a monoclonal antibody generated against MDC as detailed in Example 17. A bolus of 10 million cells from an MDC-producing clone is injected subcutaneously into the lower right quadrant of BALB/c mice. For comparison, 10 million non-transfected cells are injected into control mice. The rate and frequency of tumor formation in the two groups is compared to determine efficacy of MDC in inhibiting tumor growth. The nature of the cellular infiltrate subsequently associated with the tumor cells is identified by histologic means. In addition, recombinant MDC (20 ng) is mixed with non-transfected J558 cells and injected (20 ng/day) into tumors derived from such cells, to assay the effect of MDC administered exogenously to tumor cells.

EXAMPLE 15

Intraperitoneal Injection Assay

The cells which respond to MDC in vivo are determined through injection of 1–100 ng of purified MDC into the intraperitoneal cavity of mice, as described by Luo et al., *J. Immunol.*, 153:4616–4624 (1994). Following injection, leukocytes are isolated from peripheral blood and from the peritoneal cavity and identified by staining with the Diff Quick kit (Baxter, McGraw, Ill.). The profile of leukocytes is measured at various times to assess the kinetics of appearance of different cell types. In separate experiments, neutralizing antibodies directed against MDC (Example 17) are injected along with MDC to confirm that the infiltration of leukocytes is due to the activity of MDC.

EXAMPLE 16

In vivo Activity Assay—Subcutaneous Injection

The chemoattractant properties of MDC are assayed in vivo by adapting the protocol described by Meurer et al., *J. Exp. Med.*, 178:1913–1921 (1993). Recombinant MDC (10–500 pmol/site) is injected intradermally into a suitable mammal, e.g., dogs or rabbits. At times of 4 to 24 hours, cell infiltration at the site of injection is assessed by histologic methods. The presence of MDC is confumed by immunocytochemistry using antibodies directed against MDC. The nature of the cellular infiltrate is identified by staining with Baxter's Diff Quick kit.

EXAMPLE 17

In Vivo Myelosuppression Activity Assay

The myelosuppressive activity of MDC is assayed by injection of MDC into mice, e.g., as described by Maze et al., *J. Immunol.*, 149:1004–1009 (1992) for the measurement of the myelosuppressive action of MIP-1α. A single dose of 0.2 to 10 ug of recombinant MDC is intravenously injected into C3H/HeJ mice (Jackson Laboratories, Bar Harbor, Me.). The myelosuppressive effect of the chemokine is determined by measuring the cycling rates of myeloid progenitor cells in the femoral bone marrow and spleen. The suppression of growth and division of progenitor cells has clinical implications in the treatment of patients receiving chemotherapy or radiation therapy. The myeloprotective effect of such chemokine treatment has been demonstrated in pre-clinical models by Dunlop et al., *Blood*, 79:2221 (1992).

EXAMPLE 18

Monoclonal Antibodies to Human MDC

The following experiment, which has been initiated, is conducted to generate monoclonal antibodies to human MDC. A mouse is injected periodically with recombinant MDC (e.g., 10–20 μg emulsified in Freund's Complete Adjuvant) purified from *E. coli* as described in Example 6, purified from another recombinant host, or chemically synthesized. For a prefusion boost, the mouse is injected with MDC in PBS, and four days later the mouse is sacrificed and its spleen removed. The spleen is placed in 10 ml serum-free RPMI 1640, and a single cell suspension is formed by grinding the spleen between the frosted ends of two glass microscope slides submerged in serum-free RPMI 1640, supplemented with 2 mM L-glutamine, 1 mM sodium pyruvate, 100 units/ml penicillin, and 100 μg/ml streptomycin (RPMI) (Gibco, Canada). The cell suspension is filtered through sterile 70-mesh Nitex cell strainer (Becton Dickinson, Parsippany, N.J.), and is washed twice by centrifuging at 200 g for 5 minutes and resuspending the pellet in 20 ml serum-free RPMI. Thymocytes taken from three naive Balb/c mice are prepared in a similar manner and used as a control. NS-1 myeloma cells, kept in log phase in RPMI with 11% fetal bovine serum (FBS) (Hyclone Laboratories, Inc., Logan, Utah) for three days prior to fusion, are centrifuged at 200 g for 5 minutes, and the pellet is washed twice as described in the foregoing paragraph.

One x $10^8$ spleen cells are combined with $2.0 \times 10^7$ NS-1 cells and centrifuged, and the supernatant is aspirated. The cell pellet is dislodged by tapping the tube, and 1 ml of 37° C. PEG 1500 (50% in 75 mM Hepes, pH 8.0) (Boehringer Mannheim) is added with stirring over the course of 1 minute, followed by the addition of 7 ml of serum-free RPMI over 7 minutes. An additional 8 ml RPMI is added and the cells are centrifuged at 200 g for 10 minutes. After discarding the supernatant, the pellet is resuspended in 200 ml RPMI containing 15% FBS, 100 μM sodium hypoxanthine, 0.4 μM aminopterin, 16 μM thymidine (HAT) (Gibco), 25 units/ml IL-6 (Boehringer Mannheim) and 1.5× $10^6$ thymocytes/ml and plated into 10 Corning flat-bottom 96-well tissue culture plates (Corning, Corning, N.Y.).

On days 2, 4, and 6, after the fusion, 100 μl of medium is removed from the wells of the fusion plates and replaced with fresh medium. On day 8, the fusion is screened by ELISA, testing for the presence of mouse IgG binding to MDC as follows. Immulon 4 plates (Dynatech, Cambridge, Mass.) are coated for 2 hours at 37° C. with 100 ng/well of MDC diluted in 25 mM Tris, pH 7.5. The coating solution is aspirated and 200 ul/well of blocking solution [0.5% fish skin gelatin (Sigma) diluted in CMF-PBS] is added and incubated for 30 min. at 37° C. Plates are washed three times with PBS with 0.05% Tween 20 (PBST) and 50 μl culture supernatant is added. After incubation at 37° C. for 30 minutes, and washing as above, 50 μl of horseradish peroxidase conjugated goat anti-mouse IgG(fc) (Jackson ImmunoResearch, West Grove, Pa.) diluted 1:3500 in PBST is added. Plates are incubated as above, washed four times with PBST, and 100 μL substrate, consisting of 1 mg/ml o-phenylene diamine (Sigma) and 0.1 μl/ml 30% $H_2O_2$ in 100 mM Citrate, pit 4.5, are added. The color reaction is stopped after 5 minutes with the addition of 50 μl of 15% $H_2SO_4$. $A_{490}$ is read on a plate reader (Dynatech).

Selected fusion wells are cloned twice by dilution into 96-well plates and visual scoring of the number of colonies/ well after 5 days. The monoclonal antibodies produced by hybridomas are isotyped using the Isostrip system (Boehringer Mannheim, Indianapolis, Ind.).

The biological function of MDC, elucidated as described above, suggest several clinical applications.

First, as chemokines attract and activate monocytes and macrophages (Baggiolini et al., supra), MDC expression in a pathogenic inflammatory setting may exacerbate the disease by recruiting additional monocytes and macrophages or other leukocytes to the disease site, by activating the leukocytes that are already there, or by inducing leukocytes to remain at the site. Thus, inhibiting the chemoattractant activity of MDC may be expected to alleviate deleterious inflammatory processes. Significantly, the potential benefits of such an approach have been directly demonstrated in experiments involving IL-8, a C-X-C chemokine that attracts and activates neutrophils. Antibodies directed against IL-8 have a profound ability to inhibit inflammatory disease mediated by neutrophils [Harada et al., *J. Leukoc. Biol.*, 56:559 (1994)]. Inhibition of MDC is expected to have a similar effect in diseases in which macrophages are presumed to play a role, e.g., Crohn's disease, rheumatoid arthritis, or atherosclerosis.

Alternatively, augmenting the effect of MDC may have a beneficial role in such diseases, as chemokines have also been shown to have a positive effect in wound healing and angiogenesis. Thus, exogenous MDC or MDC agonists may be beneficial in promoting recovery from such diseases.

In addition, the myelosuppressive effect demonstrated for the C—C chemokine MIP-1α (Maze et al., supra) suggests that MDC may have a similar activity. Such activity, provided by MDC or MDC agonists, may yield substantial benefits for patients receiving chemotherapy or radiation therapy, reducing the deleterious effects of the therapy on the patient's myeloid progenitor cells.

MDC or MDC agonists may also prove to be clinically important in the treatment of tumors, as suggested by the ability of the C—C chemokine TCA3 to inhibit tumor formation in mice (see Laning et al., supra). MDC may act directly or indirectly to inhibit tumor formation, e.g., by attracting and activating various non-specific effector cells to the tumor site or by stimulating a specific anti-tumor immunity.

While the present invention has been described in terms of specific embodiments, it is understood that variations and modifications will occur to those skilled in the art. Accordingly, only such limitations as appear in the appended claims should be placed on the invention.

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
    ( A ) LENGTH: 2923 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY: CDS
    ( B ) LOCATION: 20..298

( x i ) SEQUENCE DESCRIPTION: SEQ ID NO:1:

```
GAGACATACA GGACAGAGC ATG GCT CGC CTA CAG ACT GCA CTC CTG GTT GTC        52
                    Met Ala Arg Leu Gln Thr Ala Leu Leu Val Val
                     1               5                      10

CTC GTC CTC CTT GCT GTG GCG CTT CAA GCA ACT GAG GCA GGC CCC TAC        100
Leu Val Leu Leu Ala Val Ala Leu Gln Ala Thr Glu Ala Gly Pro Tyr
            15                  20                  25

GGC GCC AAC ATG GAA GAC AGC GTC TGC TGC CGT GAT TAC GTC CGT TAC        148
Gly Ala Asn Met Glu Asp Ser Val Cys Cys Arg Asp Tyr Val Arg Tyr
        30                  35                  40

CGT CTG CCC CTG CGC GTG GTG AAA CAC TTC TAC TGG ACC TCA GAC TCC        196
Arg Leu Pro Leu Arg Val Val Lys His Phe Tyr Trp Thr Ser Asp Ser
    45                  50                  55

TGC CCG AGG CCT GGC GTG GTG TTG CTA ACC TTC AGG GAT AAG GAG ATC        244
Cys Pro Arg Pro Gly Val Val Leu Leu Thr Phe Arg Asp Lys Glu Ile
60                  65                  70                  75

TGT GCC GAT CCC AGA GTG CCC TGG GTG AAG ATG ATT CTC AAT AAG CTG        292
Cys Ala Asp Pro Arg Val Pro Trp Val Lys Met Ile Leu Asn Lys Leu
                80                  85                  90

AGC CAA TGAAGAGCCT ACTCTGATGA CCGTGGCCTT GGCTCCTCCA GGAAGGCTCA        348
Ser Gln

GGAGCCCTAC CTCCCTGCCA TTATAGCTGC TCCCCGCCAG AAGCCTGTGC CAACTCTCTG      408

CATTCCCTGA TCTCCATCCC TGTGGCTGTC ACCCTTGGTC ACCTCCGTGC TGTCACTGCC      468

ATCTCCCCCC TGACCCCTCT AACCCATCCT CTGCCTCCCT CCCTGCAGTC AGAGGGTCCT      528

GTTCCCATCA GCGATTCCCC TGCTTAAACC CTTCCATGAC TCCCACTGC  CCTAAGCTGA      588

GGTCAGTCTC CCAAGCCTGG CATGTGGCCC TCTGGATCTG GGTTCCATCT CTGTCTCCAG      648

CCTGCCCACT TCCCTTCATG AATGTTGGGT TCTAGCTCCC TGTTCTCCAA ACCCATACTA      708

CACATCCCAC TTCTGGGTCT TTGCCTGGGA TGTTGCTGAC ACTCAGAAAG TCCCACCACC      768

TGCACATGTG TAGCCCCACC AGCCCTCCAA GGCATTGCTC GCCCAAGCAG CTGGTAATTC      828

CATTTCATGT ATTAGATGTC CCCTGGCCCT CTGTCCCCTC TTAATAACCC TAGTCACAGT      888
```

| | | | | | | |
|---|---|---|---|---|---|---|
|CTCCGCAGAT|TCTTGGGATT|TGGGGGTTTT|CTCCCCCACC|TCTCCACTAG|TTGGACCAAG|948|
|GTTTCTAGCT|AAGTTACTCT|AGTCTCCAAG|CCTCTAGCAT|AGAGCACTGC|AGACAGGCCC|1008|
|TGGCTCAGAA|TCAGAGCCCA|GAAAGTGGCT|GCAGACAAAA|TCAATAAAAC|TAATGTCCCT|1068|
|CCCCTCTCCC|TGCCAAAAGG|CAGTTACATA|TCAATACAGA|GACTCAAGGT|CACTAGAAAT|1128|
|GGGCCAGCTG|GGTCAATGTG|AAGCCCCAAA|TTTGCCCAGA|TTCACCTTTC|TTCCCCCACT|1188|
|CCCTTTTTTT|TTTTTTTTTT|TTTGAGATGG|AGTTTCGCTC|TTGTCACCCA|CGCTGGAGTG|1248|
|CAATGGTGTG|GTCTTGGCTT|ATTGAAGCCT|CTGCCTCCTG|GGTTCAAGTG|ATTCTCTTGC|1308|
|CTCAGCCTCC|TGAGTAGCTG|GGATTACAGG|TTCCTGCTAC|CACGCCCAGC|TAATTTTTGT|1368|
|ATTTTTAGTA|GAGACGAGGC|TTCACCATGT|TGGCCAGGCT|GGTCTCGAAC|TCCTGTCCTC|1428|
|AGGTAATCCG|CCCACCTCAG|CCTCCCAAAG|TGCTGGGATT|ACAGGCGTGA|GCCACAGTGC|1488|
|CTGGCCTCTT|CCCTCTCCCC|ACTGCCCCCC|CCAACTTTTT|TTTTTTTTT|ATGGCAGGGT|1548|
|CTCACTCTGT|CGCCCAGGCT|GGAGTGCAGT|GGCGTGATCT|CGGCTCACTA|CAACCTCGAC|1608|
|CTCCTGGGTT|CAAGTGATTC|TCCCACCCCA|GCCTCCCAAG|TAGCTGGGAT|TACAGGTGTG|1668|
|TGCCACTACG|GCTGGCTAAT|TTTTGTATTT|TTAGTAGAGA|CAGGTTTCAC|CATATTGGCC|1728|
|AGGCTGGTCT|TGAACTCCTG|ACCTCAAGTG|ATCCACCTTC|CTTGTGCTCC|CAAAGTGCTG|1788|
|AGATTACAGG|CGTGAGCTAT|CACACCCAGC|CTCCCCCTTT|TTTTCCTAAT|AGGAGACTCC|1848|
|TGTACCTTTC|TTCGTTTTAC|CTATGTGTCG|TGTCTGCTTA|CATTTCCTTC|TCCCCTCAGG|1908|
|CTTTTTTGG|GTGGTCCTCC|AACCTCCAAT|ACCCAGGCCT|GGCCTCTTCA|GAGTACCCCC|1968|
|CATTCCACTT|TCCCTGCCTC|CTTCCTTAAA|TAGCTGACAA|TCAAATTCAT|GCTATGGTGT|2028|
|GAAAGACTAC|CTTTGACTTG|GTATTATAAG|CTGGAGTTAT|ATATGTATTT|GAAAACAGAG|2088|
|TAAATACTTA|AGAGGCCAAA|TAGATGAATG|GAAGAATTTT|AGGAACTGTG|AGAGGGGAC|2148|
|AAGGTGAAGC|TTTCCTGGCC|CTGGGAGGAA|GCTGGCTGTG|GTAGCGTAGC|GCTCTCTCTC|2208|
|TCTGTCTGTG|GCAGGAGCCA|AAGAGTAGGG|TGTAATTGAG|TGAAGGAATC|CTGGGTAGAG|2268|
|ACCATTCTCA|GGTGGTTGGG|CCAGGCTAAA|GACTGGAGT|TGGGTCTATC|TATGCCTTTC|2328|
|TGGCTGATTT|TTGTAGAGAC|GGGGTTTTGC|CATGTTACCC|AGGCTGGTCT|CAAACTCCTG|2388|
|GGCTCAAGCG|ATCCTCCTGG|CTCAGCCTCC|CAAAGTGCTG|GGATTACAGG|CGTGAATCAC|2448|
|TGCGCCTGGC|TTCCTCTTCC|TCTTGAGAAA|TATTCTTTTC|ATACAGCAAG|TATGGGACAG|2508|
|CAGTGTCCCA|GGTAAAGGAC|ATAAATGTTA|CAAGTGTCTG|GTCCTTTCTG|AGGGAGGCTG|2568|
|GTGCCGCTCT|GCAGGGTATT|TGAACCTGTG|GAATTGGAGG|AGGCCATTTC|ACTCCCTGAA|2628|
|CCCAGCCTGA|CAAATCACAG|TGAGAATGTT|CACCTTATAG|GCTTGCTGTG|GGGCTCAGGT|2688|
|TGAAAGTGTG|GGGAGTGACA|CTGCCTAGGC|ATCCAGCTCA|GTGTCATCCA|GGGCCTGTGT|2748|
|CCCTCCCGAA|CCCAGGGTCA|ACCTGCCTGC|CACAGGCACT|AGAAGGACGA|ATCTGCCTAC|2808|
|TGCCCATGAA|CGGGGCCCTC|AAGCGTCCTG|GGATCTCCTT|CTCCCTCCTG|TCCTGTCCTT|2868|
|GCCCCTCAGG|ACTGCTGGAA|AATAAATCCT|TTAAAATAGT|AAAAAAAAAA|AAAAA|2923|

( 2 ) INFORMATION FOR SEQ ID NO:2:

( i ) SEQUENCE CHARACTERISTICS:
        ( A ) LENGTH: 93 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Ala Arg Leu Gln Thr Ala Leu Leu Val Val Leu Val Leu Leu Ala
 1               5                  10                  15

Val Ala Leu Gln Ala Thr Glu Ala Gly Pro Tyr Gly Ala Asn Met Glu
            20                  25                  30

Asp Ser Val Cys Cys Arg Asp Tyr Val Arg Tyr Arg Leu Pro Leu Arg
         35                  40                  45

Val Val Lys His Phe Tyr Trp Thr Ser Asp Ser Cys Pro Arg Pro Gly
     50                  55                  60

Val Val Leu Leu Thr Phe Arg Asp Lys Glu Ile Cys Ala Asp Pro Arg
 65                  70                  75                  80

Val Pro Trp Val Lys Met Ile Leu Asn Lys Leu Ser Gln
                 85                  90
```

( 2 ) INFORMATION FOR SEQ ID NO:3:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:3:

GACACTATAG AATAGGGC                       18

( 2 ) INFORMATION FOR SEQ ID NO:4:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:4:

GTAAAACGAC GGCCAGT                       17

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:5:

AATTAACCCT CACTAAAGGG                     20

( 2 ) INFORMATION FOR SEQ ID NO:6:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:6:

GTAATACGAC TCACTATAGG GC                  22

( 2 ) INFORMATION FOR SEQ ID NO:7:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:7:

TCTATCTAGA GGCCCCTACG GCGCCAACAT GGAAG                           35

( 2 ) INFORMATION FOR SEQ ID NO:8:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:8:

CACCGGATCC TCATTGGCTC AGCTTATTGA GAA                             33

( 2 ) INFORMATION FOR SEQ ID NO:9:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:9:

AATGGATCCA CAGCACGGAG GTGACCAAG                                   29

( 2 ) INFORMATION FOR SEQ ID NO:10:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:10:

AGTCAAGCTT AGGGCACTCT GGGATCGGCA C                               31

( 2 ) INFORMATION FOR SEQ ID NO:11:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:11:

TATCGGATCC TGGTTCCGCG TGGCCCCTAC GGCGCCAACA TGGAA                45

( 2 ) INFORMATION FOR SEQ ID NO:12:

( i ) SEQUENCE CHARACTERISTICS:
        ( A ) LENGTH: 22 base pairs
        ( B ) TYPE: nucleic acid ( C ) STRANDEDNESS: single
( D ) TOPOLOGY: linear ( i i ) MOLECULE TYPE: DNA ( x i ) SEQUENCE DESCRIPTION: SEQ ID NO:12:

GAAATCCAGC AAGTATATAG CA 22

( 2 ) INFORMATION FOR SEQ ID NO:13:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:13:

ATTGCCATGG CCGGCCCCTA CGGCGCCAAC ATGGAA 36

( 2 ) INFORMATION FOR SEQ ID NO:14:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:14:

GACCAAGCTT GAGACATACA GGACAGAGCA 30

( 2 ) INFORMATION FOR SEQ ID NO:15:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:15:

TGGATCTAGA AGTTGGCACA GGCTTCTGG 29

( 2 ) INFORMATION FOR SEQ ID NO:16:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:16:

CGAAATTAAT ACGACTCACT 20

( 2 ) INFORMATION FOR SEQ ID NO:17:

( i ) SEQUENCE CHARACTERISTICS:
( A ) LENGTH: 67 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:17:

TGGATCTAGA TCAATTCAAG TCCTCCTCGC TGATCAGCTT CTGCTCTTGG CTCAGCTTAT    60

TGAGAAT    67

( 2 ) INFORMATION FOR SEQ ID NO:18:

( i ) SEQUENCE CHARACTERISTICS:
        ( A ) LENGTH: 99 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: misc_feature
        ( D ) OTHER INFORMATION: "Hu MCP-3"

( x i ) SEQUENCE DESCRIPTION: SEQ ID NO:18:

```
Met Lys Ala Ser Ala Ala Leu Leu Cys Leu Leu Thr Ala Ala Ala
 1               5                  10                  15

Phe Ser Pro Gln Gly Leu Ala Gln Pro Val Gly Ile Asn Thr Ser Thr
            20                  25                  30

Thr Cys Cys Tyr Arg Phe Ile Asn Lys Lys Ile Pro Lys Gln Arg Leu
        35                  40                  45

Glu Ser Tyr Arg Arg Thr Thr Ser Ser His Cys Pro Arg Glu Ala Val
     50                  55                  60

Ile Phe Lys Thr Lys Leu Asp Lys Glu Ile Cys Ala Asp Pro Thr Gln
65                      70                  75                  80

Lys Trp Val Gln Asp Phe Met Lys His Leu Asp Lys Lys Thr Gln Thr
                85                  90                  95

Pro Lys Leu
```

( 2 ) INFORMATION FOR SEQ ID NO:19:

( i ) SEQUENCE CHARACTERISTICS:
        ( A ) LENGTH: 99 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: misc_feature
        ( D ) OTHER INFORMATION: "Hu MCP-1"

( x i ) SEQUENCE DESCRIPTION: SEQ ID NO:19:

```
Met Lys Val Ser Ala Ala Leu Leu Cys Leu Leu Ile Ala Ala Thr
 1               5                  10                  15

Phe Ile Pro Gln Gly Leu Ala Gln Pro Asp Ala Ile Asn Ala Pro Val
            20                  25                  30

Thr Cys Cys Tyr Asn Phe Thr Asn Arg Lys Ile Ser Val Gln Arg Leu
        35                  40                  45

Ala Ser Tyr Arg Arg Ile Thr Ser Ser Lys Cys Pro Lys Glu Ala Val
     50                  55                  60

Ile Phe Lys Thr Ile Val Ala Lys Glu Ile Cys Ala Asp Pro Lys Gln
65                      70                  75                  80

Lys Trp Val Gln Asp Ser Met Asp His Leu Asp Lys Gln Thr Gln Thr
                85                  90                  95

Pro Lys Thr
```

( 2 ) INFORMATION FOR SEQ ID NO:20:

( i ) SEQUENCE CHARACTERISTICS:
        ( A ) LENGTH: 76 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: misc_feature
        ( D ) OTHER INFORMATION: "Hu MCP- 2"

( x i ) SEQUENCE DESCRIPTION: SEQ ID NO:20:

```
Gln  Pro  Asp  Ser  Val  Ser  Ile  Pro  Ile  Thr  Cys  Cys  Phe  Asn  Val  Ile
 1                   5                        10                       15

Asn  Arg  Lys  Ile  Pro  Ile  Gln  Arg  Leu  Glu  Ser  Tyr  Thr  Arg  Ile  Thr
               20                       25                       30

Asn  Ile  Gln  Cys  Pro  Lys  Glu  Ala  Val  Ile  Phe  Lys  Thr  Lys  Arg  Gly
          35                       40                       45

Lys  Glu  Val  Cys  Ala  Asp  Pro  Lys  Glu  Arg  Trp  Val  Arg  Asp  Ser  Met
 50                            55                       60

Lys  His  Leu  Asp  Gln  Ile  Phe  Gln  Asn  Leu  Lys  Pro
 65                      70                       75
```

( 2 ) INFORMATION FOR SEQ ID NO:21:

( i ) SEQUENCE CHARACTERISTICS:
        ( A ) LENGTH: 91 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: misc_feature
        ( D ) OTHER INFORMATION: "RANTES"

( x i ) SEQUENCE DESCRIPTION: SEQ ID NO:21:

```
Met  Lys  Val  Ser  Ala  Ala  Leu  Ala  Val  Ile  Leu  Ile  Ala  Thr  Ala
 1                   5                        10                       15

Leu  Cys  Ala  Pro  Ala  Ser  Ala  Ser  Pro  Tyr  Ser  Ser  Asp  Thr  Thr  Pro
               20                       25                       30

Cys  Cys  Phe  Ala  Tyr  Ile  Ala  Arg  Pro  Leu  Pro  Arg  Ala  His  Ile  Lys
          35                       40                       45

Glu  Tyr  Phe  Tyr  Thr  Ser  Gly  Lys  Cys  Ser  Asn  Pro  Ala  Val  Val  Phe
 50                            55                       60

Val  Thr  Arg  Lys  Asn  Arg  Gln  Val  Cys  Ala  Asn  Pro  Glu  Lys  Lys  Trp
 65                      70                       75                       80

Val  Arg  Glu  Tyr  Ile  Asn  Ser  Leu  Glu  Met  Ser
                    85                       90
```

( 2 ) INFORMATION FOR SEQ ID NO:22:

( i ) SEQUENCE CHARACTERISTICS:
        ( A ) LENGTH: 91 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: misc_feature ( D ) OTHER INFORMATION: "MIP-1"

( x i ) SEQUENCE DESCRIPTION: SEQ ID NO:22:

| Met | Lys | Leu | Cys | Val | Thr | Val | Leu | Ser | Leu | Leu | Met | Leu | Val | Ala | Ala |
| 1 | | | | 5 | | | | | 10 | | | | | 15 | |
| Phe | Cys | Ser | Pro | Ala | Leu | Ser | Ala | Pro | Met | Gly | Ser | Asp | Pro | Pro | Thr |
| | | | 20 | | | | | 25 | | | | | 30 | | |
| Ala | Cys | Cys | Phe | Ser | Tyr | Thr | Arg | Glu | Ala | Ser | Ser | Asn | Phe | Val | Val |
| | | 35 | | | | | 40 | | | | | 45 | | | |
| Asp | Tyr | Tyr | Glu | Thr | Ser | Ser | Leu | Cys | Ser | Gln | Pro | Ala | Val | Val | Phe |
| | 50 | | | | | 55 | | | | | 60 | | | | |
| Gln | Thr | Lys | Arg | Ser | Lys | Gln | Val | Cys | Ala | Asp | Pro | Ser | Glu | Ser | Trp |
| 65 | | | | | 70 | | | | | 75 | | | | | 80 |
| Val | Gln | Glu | Tyr | Val | Tyr | Asp | Leu | Glu | Leu | Asn | | | | | |
| | | | | 85 | | | | | 90 | | | | | | |

( 2 ) INFORMATION FOR SEQ ID NO:23:

( i ) SEQUENCE CHARACTERISTICS:
( A ) LENGTH: 92 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: misc_feature
( D ) OTHER INFORMATION: "MIP-1"

( x i ) SEQUENCE DESCRIPTION: SEQ ID NO:23:

| Met | Gln | Val | Ser | Thr | Ala | Ala | Leu | Ala | Val | Leu | Leu | Cys | Thr | Met | Ala |
| 1 | | | | 5 | | | | | 10 | | | | | 15 | |
| Leu | Cys | Asn | Gln | Phe | Ser | Ala | Ser | Leu | Ala | Ala | Asp | Thr | Pro | Thr | Ala |
| | | | 20 | | | | | 25 | | | | | 30 | | |
| Cys | Cys | Phe | Ser | Tyr | Thr | Ser | Arg | Gln | Ile | Pro | Gln | Asn | Phe | Ile | Ala |
| | | 35 | | | | | 40 | | | | | 45 | | | |
| Asp | Tyr | Phe | Glu | Thr | Ser | Ser | Gln | Cys | Ser | Lys | Pro | Gly | Val | Ile | Phe |
| | 50 | | | | | 55 | | | | | 60 | | | | |
| Leu | Thr | Lys | Arg | Ser | Arg | Gln | Val | Cys | Ala | Asp | Pro | Ser | Glu | Glu | Trp |
| 65 | | | | | 70 | | | | | 75 | | | | | 80 |
| Val | Gln | Lys | Tyr | Val | Ser | Asp | Leu | Glu | Leu | Ser | Ala | | | | |
| | | | | 85 | | | | | 90 | | | | | | |

( 2 ) INFORMATION FOR SEQ ID NO:24:

( i ) SEQUENCE CHARACTERISTICS:
( A ) LENGTH: 96 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: misc_feature
( D ) OTHER INFORMATION: "I-309"

( x i ) SEQUENCE DESCRIPTION: SEQ ID NO:24:

| Met | Gln | Ile | Ile | Thr | Thr | Ala | Leu | Val | Cys | Leu | Leu | Leu | Ala | Gly | Met |
| 1 | | | | 5 | | | | | 10 | | | | | 15 | |
| Trp | Pro | Glu | Asp | Val | Asp | Ser | Lys | Ser | Met | Gln | Val | Pro | Phe | Ser | Arg |
| | | | 20 | | | | | 25 | | | | | 30 | | |

|     |     |           |     |     |     |     |           |     |     |     |     |           |     |     |     |
|-----|-----|-----------|-----|-----|-----|-----|-----------|-----|-----|-----|-----|-----------|-----|-----|-----|
| Cys | Cys | Phe<br>35 | Ser | Phe | Ala | Glu | Gln<br>40 | Glu | Ile | Pro | Leu | Arg<br>45 | Ala | Ile | Leu |
| Cys | Tyr<br>50 | Arg | Asn | Thr | Ser | Ser<br>55 | Ile | Cys | Ser | Asn | Glu<br>60 | Gly | Leu | Ile | Phe |
| Lys<br>65 | Leu | Lys | Arg | Gly | Lys<br>70 | Glu | Ala | Cys | Ala | Leu<br>75 | Asp | Thr | Val | Gly | Trp<br>80 |
| Val | Gln | Arg | His | Arg<br>85 | Lys | Met | Leu | Arg | His<br>90 | Cys | Pro | Ser | Lys | Arg<br>95 | Lys |

What is claimed is:

1. A hybridoma cell line producing a monoclonal antibody that is specifically reactive with MDC.

2. The monoclonal antibody produced by the hybridoma of claim 1.

3. An antibody specifically reactive with a polypeptide of SEQ ID NO: 2.

4. An antibody according to claim 3 which is a monoclonal antibody.

5. A hybridoma cell line producing the antibody of claim 4.

6. Polyclonal antisera comprising an antibody according to claim 3.

7. An antibody specifically reactive with an MDC polypeptide, said polypeptide comprising a sequence of amino acids identified by positions 25 to 93 of SEQ ID NO: 2.

8. An antibody according to claim 7 which is a monoclonal antibody.

9. A hybridoma cell line producing the antibody of claim 8.

10. Polyclonal antisera comprising an antibody according to claim 7.

* * * * *

UNITED STATES PATENT AND TRADEMARK OFFICE
CERTIFICATE OF CORRECTION

PATENT NO. : 5,688,927

DATED : November 18, 1997

INVENTOR(S) : Godiska et al.

It is certified that error appears in the above-identified patent and that said Letters Patent is hereby corrected as shown below:

Cover page, under "Other Publications - Chang *et al.*", please delete "$\lambda$" and insert --$\gamma$--.

Cover page (continued), under "Other Publications - Kurjan *et al.*," please delete "1992" and insert --1982--.

Cover page (continued), under Other Publications - Tjoelker *et al.*," please delete "Aceytlhydrolase" and insert --Acetylhydrolase--.

Column 14, line 8, please delete "Pd:" and insert --Pel:--.

Signed and Sealed this

Nineteenth Day of October, 1999

Q. TODD DICKINSON

Attest:

Attesting Officer          Acting Commissioner of Patents and Trademarks